(12) United States Patent
Uwabu et al.

(10) Patent No.: US 11,237,153 B2
(45) Date of Patent: Feb. 1, 2022

(54) METHOD FOR PREDICTING AMOUNT OF ANALYTE IN URINE SPECIMEN

(71) Applicant: ARKRAY, Inc., Kyoto (JP)

(72) Inventors: Masashi Uwabu, Tokyo (JP);
Masakazu Sawanobori, Tokyo (JP);
Koichi Fujimoto, Kyoto (JP); Jun Kamito, Kyoto (JP); Akitsugu Kudo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 18 days.

(21) Appl. No.: 15/077,115

(22) Filed: Mar. 22, 2016

(65) Prior Publication Data

US 2016/0282329 A1   Sep. 29, 2016

(30) Foreign Application Priority Data

Mar. 23, 2015 (JP) .............................. JP2015-059887
Mar. 18, 2016 (JP) .............................. JP2016-055988

(51) Int. Cl.
*G01N 33/493* (2006.01)
*G01N 33/84* (2006.01)

(52) U.S. Cl.
CPC ........... *G01N 33/493* (2013.01); *G01N 33/84* (2013.01); *G01N 2560/00* (2013.01)

(58) Field of Classification Search
CPC .. G01N 2560/00; G01N 33/493; G01N 33/84; G01N 33/48
See application file for complete search history.

(56) References Cited

FOREIGN PATENT DOCUMENTS

| EP | 0 740 252 A2 | 10/1996 |
|---|---|---|
| JP | 2010-230618 A | 10/2010 |
| JP | 2013-181019 A | 9/2013 |
| JP | 2013-181932 A | 9/2013 |
| WO | WO 2009/078950 A2 | 6/2009 |
| WO | WO 2009/078950 A3 | 6/2009 |

OTHER PUBLICATIONS

Anne-Michelle Ruha, "Recommendations for Provoked Challenge Urine Testing", Journal of Medical Toxicology: Official Journal of the American college of Medical Toxicology, vol. 9, No. 4, pp. 318-325, 2013.
Eleonor Blaucok-Busch et al., "Efficacy of DMSA Therapy in a Sample of Arab Children with Autistic Spectrum Disorder", M dica, vol. 7. No. 3, pp. 214-221, 2012.
Extended European Search Report of the corresponding European Application (No. 16161602.4) dated Jul. 28, 2016.
Jun Lu et al., "Triethylenetetramine and Metabolites: Levels in Relation to Copper and Zinc Excretion in Urine of Healthy Volunteers and Type 2 Diabetic Patients", Drug Metabolism and Disposition, vol. 35, No. 2, pp. 221-227, 2006.
Pangborn, "Mechanisms of Detoxication and Procedures for Dextoxification", Doctor's Data Inc., pp. 126-142, 1994.
Office Action received in European Patent Application No. 16 161 602.4 dated Mar. 17, 2017.
Office Action issued in JP application No. 2016-055988, dated Nov. 19, 2019.

*Primary Examiner* — Samuel P Siefke
(74) *Attorney, Agent, or Firm* — Knobbe, Martens, Olson & Bear, LLP

(57) ABSTRACT

A method predicts an amount of an analyte in a urine specimen collected in a target time zone. The method includes measuring an amount of an analyte in a urine specimen collected in a predetermined time zone after an administration of a chelating agent and b) predicting, from the measured amount of the analyte in the urine specimen collected in the predetermined time zone, the amount of the analyte in the urine specimen collected in the target time zone on the basis of a correlation between amounts of analyte in urine specimens in the predetermined time zone and amounts of analyte in urine specimens in the target time zone. The amounts of the analyte in the urine specimens in the predetermined time and the target time zone are measured before predicting the amount of the analyte in the urine specimen collected in the target time zone.

5 Claims, No Drawings

METHOD FOR PREDICTING AMOUNT OF ANALYTE IN URINE SPECIMEN

CROSS-REFERENCE TO RELATED APPLICATIONS

This application claims priority to Japanese Patent Application No. 2015-059887 filed on Mar. 23, 2015 and Japanese Patent Application No. 2016-055988 filed on Mar. 18, 2016, the disclosure of which including the specification, the drawings, and the claims is hereby incorporated by reference in its entirety.

BACKGROUND OF THE INVENTION

Field of the Invention

The present invention relates to a method for predicting the amount of an analyte in a urine specimen.

Description of the Related Art

Toxic metals are taken in a living body on a day-to-day basis through foods, water, exhaust gas in the air, etc. It is considered that the toxic metals accumulated in a living body cause various diseases and various unidentified complaints. Thus, attempts have been made to excrete a toxic metal in the body by administering a chelating agent that chelates with the toxic metal (Non-Patent Document 1). In order to check the effect of the administration of the chelating agent, the concentration of the toxic metal contained in urine is measured after the administration of the chelating agent.

However, the concentration of a toxic metal in urine changes depending on the time at which the urine is collected. Thus, in the measurement of the concentration of a toxic metal, it is necessary to collect and accumulate urine over a long time (e.g., 6 hours) after the administration of a chelating agent and to measure the concentration of the toxic metal in the accumulated urine, for example. Thus, a subject has to collect urine continuously over a long time, which places a considerable burden on the subject.

CITATION LIST

Non-Patent Document

[Non-Patent Document 1] Jon B. Pangborn, "MECHANISMS OF DETOXICATION AND PROCEDURES FOR DETOXIFICATION", Doctor's DATA INC., 1994, pp. 126-142

SUMMARY OF THE INVENTION

With the foregoing in mind, it is an object of the present invention to provide a prediction method that enables easy prediction of the amount of an analyte in a urine specimen in a target time zone after administration of a chelating agent.

In order to solve the above-described problem, the present invention provides a method for predicting the amount of an analyte in a urine specimen (also referred to simply as a "prediction method" hereinafter), including the step of: predicting, from a measured amount of an analyte in a urine specimen collected in a predetermined time zone after administration of a chelating agent, the amount of the analyte in a urine specimen collected in a target time zone after the administration of the chelating agent on the basis of a correlation, wherein the correlation is a correlation between measured amounts of the analyte in urine specimens in the predetermined time zone and measured amounts of the analyte in urine specimens in the target time zone.

According to the prediction method of the present invention, the amount of an analyte in a urine specimen in a target time zone after administration of a chelating agent can be predicted easily.

DETAILED DESCRIPTION OF THE INVENTION

Method for Predicting Analyte in Urine Specimen

The method for predicting the amount of an analyte in a urine specimen according to the present invention is, as described above, a method for predicting the amount of analyte in a urine specimen, including the step of: predicting, from a measured amount of an analyte in a urine specimen collected in a predetermined time zone after administration of a chelating agent, the amount of the analyte in a urine specimen collected in a target time zone after the administration of the chelating agent on the basis of a correlation, wherein the correlation is a correlation between measured amounts of the analyte in urine specimens in the predetermined time zone and measured amounts of the analyte in urine specimens in the target time zone. The prediction method of the present invention is characterized in that, as the correlation, a correlation between measured amounts of the analyte in urine specimens in the predetermined time zone and measured amounts of the analyte in urine specimens in the target time zone is used, and other steps and conditions are not particularly limited.

Generally, in order to analyze an analyte in a urine specimen, urine has to be collected and accumulated over a long time of about 6 hours after the administration of a chelating agent, as disclosed in the prior art document, for example. Then, the amount of the analyte in the accumulated urine (pooled urine) is measured, and evaluation is made on the basis of "the measured value obtained through measurement on urine accumulated for a long time". That is, at present, the measured value obtained through measurement on urine accumulated for a long time serves as a basis for the evaluation. However, the inventors of the present invention found out that measured amounts of an analyte in urine specimens collected in a predetermined time zone after the administration of a chelating agent (also referred to simply as "measured amounts in a predetermined time zone" hereinafter) correlate with measured amounts of the analyte in urine specimens collected in a target time zone after the administration of the chelating agent (also referred to simply as "measured amounts in a target time zone" hereinafter). Thus, according to the present invention, through the measurement on urine collected over a predetermined time period (which is a short time, for example), it is possible to predict the measured amount in a target time zone (which is a long time, for example). Therefore, according to the present invention, it is not necessary to collect and accumulate urine over a long time, for example.

In the present invention, the analyte is not particularly limited, and may be a metal, a chemical substance, or the like, for example. The metal is not particularly limited, and examples thereof include metals such as aluminum (Al), antimony (Sb), arsenic (As), barium (Ba), beryllium (Be), bismuth (Bi), cadmium (Cd), cesium (Cs), gadolinium (Gd), lead (Pb), mercury (Hg), nickel (Ni), palladium (Pd), platinum (Pt), tellurium (Te), thallium (Tl), thorium (Th), tin (Sn), tungsten (W), and uranium (U). Examples of the chemical substance include reagents, agricultural chemicals, and cosmetics. The chemical substance may be chelated by a chelating agent. One kind of analyte may be measured, or two or more kinds of analytes may be measured, for example.

In the present invention, the chelating agent is not particularly limited, and can be determined as appropriate depending on the analyte, for example. Examples of the chelating agent include dithizone, tiopronin, meso-2,3-dimercaptosuccinic acid (DMSA), 2,3-dimercapto-1-propanesulfonic acid sodium salt (DMPS), ethylenediaminetetraacetic acid (EDTA), nitrilotriacetic acid (NTA), ethylene diamine-N,N'-disuccinic acid (EDDS), α-lipoic acid, diethylenetriaminepentaacetic acid (DTPA), penicillamine, dimercaprol, glutathione, phytic acid, chitosan, citric acid, quercetin, and ascorbic acid. Among them, EDTA, tiopronin, DMSA, and DMPS are preferable. One kind of chelating agent may be used alone, or two or more kinds of chelating agent may be used in combination, for example. The combination of the chelating agent and the analyte is not particularly limited, and examples thereof include the combinations of: EDTA with mercury and lead; tiopronin with mercury; and DMSA with mercury, cadmium, and lead. In each of the above-listed combinations, the chelating agent may be used in combination with one kind of the analyte or two or more kinds of the analytes.

In the present invention, the predetermined time zone is a time zone different from the target time zone (time range). It is only required that, for example, the predetermined time zone is not the same as the target time zone, and the predetermined time zone may overlap partially with the target time zone, for example. The predetermined time zone is not particularly limited, and can be set as appropriate depending on the analyte and the chelating agent, for example. From the viewpoint of alleviating the burden of urine specimen collection, for example, the predetermined time zone preferably is from 0 to 6 hours, 0 to 3 hours, 0 to 2 hours, 0 to 1.5 hours, 0 to 1 hour, or 0 to 0.5 hours after the administration of the chelating agent. Also, from the viewpoint of further improving the accuracy in predicting the amount of the analyte, for example, the predetermined time zone preferably is from 0 to 0.5 hours, 0 to 1 hour, 0 to 1.5 hours, 0 to 2 hours, 0 to 3 hours, or 0 to 6 hours after the administration of the chelating agent.

The combination of the analyte, the chelating agent, and the predetermined time zone is not particularly limited. For example, when the analyte is a metal and the chelating agent is EDTA, the predetermined time zone is, for example, from 0 to 0.5 hours, 0 to 1 hour, 1 to 1.5 hours, or 0 to 2 hours after the administration of the chelating agent. When the analyte is a metal and the chelating agent is tiopronin, the predetermined time zone is, for example, from 0 to 0.5 hours, 0 to 1 hour, 1 to 1.5 hours, or 0 to 2 hours after the administration of the chelating agent. When the analyte is a metal and the chelating agent is DMSA, the predetermined time zone is, for example, from 0 to 0.5 hours, 0 to 1 hour, 1 to 1.5 hours, or 0 to 2 hours after the administration of the chelating agent.

In the present invention, the target time zone is not particularly limited, and may be a time zone for which it is desired to predict the amount of an analyte, for example. The target time zone is, for example, from 0 to 24 hours, 0 to 12 hours, or 0 to 6 hours after the administration of the chelating agent. The target time zone is a time range, for example. The target time zone may be, for example, a time zone in which the measured amount of the analyte in a urine specimen generally is evaluated after the administration of the chelating agent (also referred to as a "reference time" hereinafter). Specifically, when the analyte is a metal, the reference time is, for example, from 0 to 24 hours, 0 to 12 hours, or 0 to 6 hours after the administration of the chelating agent.

The predetermined time zone preferably is shorter than the target time zone, from the viewpoint of alleviating the burden of urine specimen collection, for example. The ratio (P:S) between the target time zone (P) and the predetermined time zone (S) is not particularly limited, and is, for example, 1:0.0042 to 0.125, 1:0.0042 to 0.25, or 1:0.0042 to 0.5, and preferably is 1:0.083 to 0.5. The combination of the target time zone and the predetermined time zone is not particularly limited. When the target time zone is from 0 to 6 hours, the predetermined time zone is, for example, from 0 to 1 hour, 0 to 0.5 hours, 0.5 to 1 hour, 0.1 to 3 hours, 0.5 to 3 hours, or 1 to 2 hours. When the target time zone is from 0 to 12 hours, the predetermined time zone is, for example, from 0.1 to 3 hours. When the target time zone is from 0 to 24 hours, the predetermined time zone is, for example, 0.1 to 3 hours.

The prediction method of the present invention may further include the step of determining the measured amount of the analyte in the urine specimen collected in the predetermined time zone after the administration of the chelating agent. A subject to which the chelating agent is administered (referred to as an "administration subject" hereinafter) is not particularly limited, and may be a human, a non-human animal, or the like, for example. Examples of the non-human animal include mammals excluding humans.

The dose of the chelating agent, the number of times the chelating agent is administered, and the administration method can be set as appropriate depending on the chelating agent, the administration subject, and the like. Examples of the administration method include intravenous injection, intramuscular injection, subcutaneous injection, intradermal injection, oral administration, transdermal administration, rectal administration, intraperitoneal administration, and local administration. Specifically, when the chelating agent is EDTA and the administration subject is a human, the dose is 1 to 3 g and the administration method is intravenous injection or oral administration, for example. When the chelating agent is tiopronin and the administration subject is a human, the dose is 100 to 500 mg and the administration method is oral administration, for example. When the chelating agent is DMSA and the administration subject is a human, the dose is 100 to 500 mg and the administration method is oral administration, for example.

The method for collecting the urine specimen is not particularly limited, and any known urine collection method can be used, for example. The urine specimen may be obtained by, for example, collecting urine discharged by the administration subject or collecting urine from the bladder or the like of the administration subject using a medical device such as a catheter. The collected urine may be used as it is as the urine specimen. Alternatively, an antiseptic agent supplied with a urine storing bag or the like may be added to the collected urine, and the resultant mixture may be used as the urine specimen.

The number of times the urine specimen is collected in the predetermined time zone (also referred to simply as "the number of collections in the predetermined time" hereinafter) is not particularly limited, and can be set as appropriate depending on the method for collecting the urine specimen, for example. The number of collections in the predetermined time zone may be once, or two or more times, for example.

In the latter case, for example, urine specimens collected at the respective times may be subjected to measurement as separate urine specimens, or a mixture of the urine specimens collected at the respective times may be subjected to measurement as a single urine specimen (also referred to as "accumulated urine" hereinafter). In the case where the discharged urine is to be collected, the number of collections in the predetermined time zone can be set as appropriate depending on the frequency of urination by the administration subject. The number of collections in the predetermined time zone is once when urine is discharged once in the predetermined time zone, for example. When urine is discharged two or more times in the predetermined time zone, the number of collections in the predetermined time zone may be once, two or more times, or equal to the number of times the urine is discharged.

The method for measuring the analyte in the urine specimen is not particularly limited, and can be determined as appropriate depending on the kind of the analyte, for example. When the analyte is a metal, the method for measuring the analyte may be an atomic absorption method, plasma emission spectrometry, plasma mass spectrometry, chelatometry, or the like, for example. When the analyte is a chemical substance, the method for measuring the analyte may be absorptiometry, high performance liquid chromatography (HPLC), or the like, for example.

The measured amount of the analyte is not particularly limited, and may be a measured value obtained by the method for measuring the analyte, a value calculated from the measured value, or the like, for example. Examples of the value calculated from the measured value include the weight of the analyte, the concentration of the analyte, and the weight of the analyte per urine collection time.

In the case where the separate urine specimens are used as the urine specimens, the measured amount of the analyte may be, for example, the mean value of the measured amounts of the analyte in two or more of the urine specimens or the measured amount of the analyte in any one of the urine specimens.

The measured amount of the analyte may be the measured amount of the analyte corrected with an internal standard in the urine specimen. The internal standard is not particularly limited, and may be creatinine, the specific gravity of the urine specimen, or the like, for example. The correction using the internal standard is not particularly limited, and may be, for example, correction to the measured value with reference to the weight, the concentration, or the like of the internal standard.

In the prediction step, the amount of the analyte in a urine specimen collected in a target time zone after the administration of the chelating agent is predicted on the basis of the correlation. The correlation may be, for example, a correlation equation prepared from the measured amounts of the analyte in urine specimens in the predetermined time zone and the measured amounts of the analyte in the target time zone. Hereinafter, the amount of an analyte in a urine specimen collected in a target time zone predicted indirectly by the prediction method of the present invention is referred to as the "estimated measured amount of the analyte", and the measured amount of an analyte in a urine specimen collected in a target time zone obtained by the method disclosed in the above-listed prior art document is referred to as the "true measured amount of the analyte". An example where the amount of an analyte is predicted by preparing a correlation equation will be described below. The correlation equation can be prepared in the following manner, for example. Specifically, regarding a plurality of administration subjects, the true amounts of the analyte are measured beforehand by the method disclosed in the prior art document. On the other hand, regarding the same administration subjects, the measured amounts of the analyte in urine specimens collected in a predetermined time zone after the administration of a chelating agent are measured by the above-described measurement method. The correlation equation can be prepared by analyzing the measured amounts obtained in both the cases. Then, by substituting the measured amount of the analyte in a urine specimen of an administration subject collected in the predetermined time zone into the thus-prepared correlation equation, the estimated measured amount of the analyte can be predicted indirectly.

The amount of the analyte is not particularly limited, and may be the weight of the analyte, the concentration of the analyte, the weight of the analyte per urine collection time, or the like, for example. The unit of the amount of the analyte may be the same as or different from the unit of the measured amount of the analyte. The amount of the analyte may be the amount of the analyte corrected with an internal standard in the urine specimen.

Method for Evaluating Possibility of Analyte Excretion

A method for evaluating the possibility of analyte excretion according to the present invention (also referred to simply as an "evaluation method" hereinafter) includes the step of: evaluating the possibility of analyte excretion by providing, as an analyte excretion marker, a measured amount of an analyte in a urine specimen collected in a predetermined time zone after administration of a chelating agent, and comparing the analyte excretion marker with a reference value (the evaluation step). The evaluation method according to the present invention is characterized in that it uses a measured amount of an analyte in a urine specimen collected in a predetermined time zone after administration of a chelating agent as an analyte excretion marker and evaluates the possibility of analyte excretion by comparing the analyte excretion marker with a reference value, and other steps and conditions are not particularly limited. Regarding the evaluation method of the present invention, reference can be made to the above description concerning the prediction method of the present invention, for example.

As described above, heretofore, evaluation of analyte excretion is made on the basis of the measured value obtained through measurement on urine accumulated for a long time. However, as described above, the inventors of the present invention found out that measured amounts in a predetermined time zone correlate with measured amounts in a target time zone. Accordingly, it was also found that, for example, the analyte excretion can be evaluated on the basis of the measured amount in the predetermined time zone, instead of the measured amount in the target time zone (e.g., the measured value obtained through measurement on urine accumulated for a long time). Thus, according to the evaluation method of the present invention, the possibility of analyte excretion can be evaluated through the measurement on urine collected over a predetermined time period (which is a short time, for example), for example. Therefore, the evaluation method of the present invention can evaluate the possibility of analyte excretion easily.

The reference value is not particularly limited. For example, the reference value may be set on the basis of the measured amounts of the analyte in a plurality of urine specimens, or may be set on the basis of the index value used for the measured amount of the analyte in a urine specimen collected in a known reference time. In the latter case, on the basis of the correlation between the measured amount of the analyte in the urine specimen collected in the reference time and the measured amount of the analyte in the urine specimen collected in the predetermined time zone, the reference value can be calculated from the index value, for example.

In the evaluation step, the method for evaluating the analyte excretion is not particularly limited. For example, when the excretion marker in the urine specimen is equal to or greater than the reference value, it can be evaluated that the analyte may have been excreted or the analyte is likely to have been excreted. When the excretion marker in the urine specimen is significantly lower than the reference value, it can be evaluated that the analyte may not have been excreted or is not likely to have been excreted.

EXAMPLES

Next, examples of the present invention will be described. It is to be noted, however, that the present invention is by no means limited by the following examples.

Example 1

The present example examined whether the measured amounts of analytes in urine specimens collected in predetermined time zones after administration of a chelating agent correlate with the measured amounts of the analytes in urine specimens collected in a time zone different from the predetermined time zones.

Example 1-1

Example 1-1 examined whether the measured amounts of analytes in urine specimens collected in predetermined time zones after administration of EDTA correlate with the measured amounts of the analytes in urine specimens collected in a target time zone.

(1) Collection of Urine Specimens

Five subjects were instilled with an infusion containing 2 g of EDTA calcium (Bleian I.V. Infusion 1 g, Nissin Pharmaceutical Co., Ltd.) over 1 hour. From each of the subjects, urines in predetermined time zones (0 to 0.5 hours, 0 to 1 hour, 0 to 1.5 hours, and 0 to 2 hours) after the instillation were collected and accumulated to provide urine specimens. The target time zone was set to 0 to 6 hours after the instillation. From each of the subjects, urines 0 to 6 hours after the instillation were collected and accumulated to provide urine specimens.

(2) Analysis of Analytes

Regarding each of the urine specimens, the concentration of mercury as an analyte was measured using a reduced vaporized atomic absorption spectrometer (MERCURY ANALYZER, Nippon Instruments Corporation). Also, regarding each of the urine specimens, the concentration of lead as another analyte was measured by atomic absorption analysis using a flameless atomic absorption spectrophotometer (SpectrAA-220Z, VARIAN). Then, regarding each of the urine specimens, the concentration of creatinine was measured using a creatinine measurement kit (Aqua-auto Kainos CRE-II Reagent, KAINOS Laboratories, Inc.) and a measurement device (JCA-BM1650 automated analyzer BioMajesty, JEOL Ltd.). The measurement of the lead concentration and the creatinine concentration was outsourced to FALCO HOLDINGS Co., Ltd. Subsequently, regarding the respective urine specimens, the concentrations of the analytes were divided with the corresponding creatinine concentrations to calculate the corrected concentrations of the analytes. Then, on the basis of the data obtained regarding the urine specimens, the correlation equation expressing the correlation between the creatinine-corrected concentrations of each analyte in the urine specimens collected in each predetermined time zone (also referred to as "the creatinine-corrected concentrations in each predetermined time zone" hereinafter) and the creatinine-corrected concentrations of the analyte in the urine specimens collected in the target time zone (the true measured amounts of the analyte) (also referred to as "the creatinine-corrected concentrations in the target time zone" hereinafter) was determined, and the correlation coefficient was calculated.

The results thereof are shown in Table 1. As can be seen from Table 1, when the analyte was mercury or lead, the measured amounts (y) of the analyte in the urine specimens collected in each predetermined time zone exhibited a high correlation with the true measured amounts (x) of the analyte. Also, estimated measured amounts of the analyte were predicted from the measured amounts of the analyte in the urine specimens collected in each predetermined time zone on the basis of the corresponding correlation equation. As a result, the estimated measured amounts of the analyte were very similar to the corresponding true measured amounts of the analyte. From these results, it was found that the measured amount of an analyte in a urine specimen collected in a predetermined time zone shows a high correlation with the measured amount of an analyte in a urine specimen collected in another time zone. It was also found that the amount of an analyte in a urine specimen collected in a target time zone can be predicted on the basis of the correlation between the measured amount of the analyte in a urine specimen collected in a predetermined time zone and the measured amount of the analyte in a urine specimen collected in a target time zone.

TABLE 1

|  | Correlation coefficient (correlation equation) for 0 to 0.5 hr | Correlation coefficient (correlation equation) for 0 to 1 hr | Correlation coefficient (correlation equation) tor 0 to 1.5 hr | Correlation coefficient (correlation equation) for 0 to 2 hr |
|---|---|---|---|---|
| Mercury (Hg) | 0.961 (y = 2.3569x − 2.3365) | 0.980 (y = 4.0676x − 2.5836) | 0.981 (y = 3.622x − 1.9411) | 0.977 (y = 2.9646x − 1.7872) |
| Lead (Pb) | 0.718 (y = 0.3217x + 0.6774) | 0.732 (y = 0.3805x + 6.2543) | 0.789 (y = 0.9709x − 0.2578) | 0.831 (y = 1.2194 − 3.4266) |

Example 1-2

Example 1-2 examined whether the measured amounts of analytes in urine specimens collected in predetermined time zones after administration of tiopronin correlate with the measured amounts of the analytes in urine specimens collected in a target time zone.

(1) Collection of Urine Specimens

An oral medicine containing 400 mg of tiopronin (Thiola 100, Mylan Inc.) was administered orally to five subjects. From each of the subjects, urines in predetermined time zones (0 to 1 hour, 0 to 2 hours, and 0 to 3 hours) after the administration were collected and accumulated to provide urine specimens. The target time zone was set to 0 to 6 hours after the administration. From each of the subjects, urines 0 to 6 hours after the administration were collected and accumulated to provide urine specimens.

(2) Analysis of Analytes

Regarding each of the urine specimens, the concentrations of aluminum, arsenic, barium, cadmium, cesium, mercury, nickel, thallium, tin, and tungsten as analytes were measured by inductively coupled plasma mass spectrometry (ICP-MS). Also, regarding each of the urine specimens, the concentration of creatinine was measured by the Jaffe's method. The measurement of the concentrations of the analytes and the creatinine was outsourced to Doctor's Data, Inc. Subsequently, the concentrations of the analytes were divided with the corresponding creatinine concentrations to calculate the corrected concentrations of the analytes. Then, on the basis of the data obtained regarding the urine specimens, the correlation equation expressing the correlation between the creatinine-corrected concentrations in each predetermined time zone and the creatinine-corrected concentrations in the target time zone was determined, and the correlation coefficient was calculated.

The results thereof are shown in Table 2. As can be seen from Table 2, when the analyte was aluminum, arsenic, barium, cadmium, cesium, mercury, nickel, thallium, tin, or tungsten, the measured amounts (y) of the analyte in the urine specimens collected in each predetermined time zone exhibited a high correlation with the true measured amounts (x) of the analyte. Also, estimated measured amounts of the analyte were predicted from the measured amounts of the analyte in the urine specimens collected in each predetermined time zone on the basis of the corresponding correlation equation. As a result, the estimated measured amounts of the analyte were very similar to the corresponding true measured amounts of the analyte. From these results, it was found that the measured amount of an analyte in a urine specimen collected in a predetermined time zone shows a high correlation with the measured amount of an analyte in a urine specimen collected in another time zone. It was also found that the amount of an analyte in a urine specimen collected in a target time zone can be predicted on the basis of the correlation between the measured amount of the analyte in a urine specimen collected in a predetermined time zone and the measured amount of the analyte in a urine specimen collected in a target time zone.

TABLE 2

|  | Correlation coefficient (correlation equation) for 0 to 1 hr | Correlation coefficient (correlation equation) for 0 to 2 hr | Correlation coefficient (correlation equation) for 0 to 3 hr |
| --- | --- | --- | --- |
| Aluminum (Al) | — | 0.633 (y = 1.412x + 3.050) | 0.702 (y = 1.080x + 3.777) |
| Arsenic (As) | 0.957 (y = 1.0487x − 3.7106) | 0.983 (y = 1.017x + 5.341) | 0.993 (y = 0.983x − 5.230) |
| Barium (Ba) | 0.866 (y = 0.8021x + 0.5258) | 0.956 (y = 1.027x + 0.302) | 0.959 (y = 0.698x + 0.700) |
| Cadmium (Cd) | 0.852 (y = 1.1429x + 0.1886) | 0.878 (y = 1.480x − 0.072) | 0.867 (y = 1.439x − 0.060) |
| Cesium (Cs) | 0.927 (y = 0.9224x + 1.2037) | 0.921 (y = 1.009x + 0.803) | 0.912 (y = 0.965x + 0.935) |
| Mercury (Hg) | 0.857 (y = 2.6832x − 0.7462) | 0.967 (y = 2.5708x − 13.472) | 0.976 (y = 1.9542x − 9.5809) |
| Nickel (Ni) | 0.805 (y = 0.9522x + 0.5576) | 0.816 (y = 1.072x + 0.426) | 0.814 (y = 1.185x + 0.180) |

TABLE 2-continued

|  | Correlation coefficient (correlation equation) for 0 to 1 hr | Correlation coefficient (correlation equation) for 0 to 2 hr | Correlation coefficient (correlation equation) for 0 to 3 hr |
| --- | --- | --- | --- |
| Thallium (Tl) | 1.000 (y = x + 0.1) | 0.972 (y = 0.884x + 0.104) | 0.990 (y = 0.930x + 0.067) |
| Tin (Sn) | 0.899 (y = 1.3333x − 0.0067) | 0.943 (y = 1.027x + 0.090) | 0.920 (y = 1.071x + 0.100) |
| Tungsten (W) | 0.980 (y = 1.8191x − 0.0383) | 0.980 (y = 1,607x − 0.034) | 0.985 (y = 1.400x − 0.015) |

Example 1-3

Example 1-3 examined whether the measured amounts of analytes in urine specimens collected in predetermined time zones after administration of DMSA correlate with the measured amounts of the analytes in urine specimens collected in a target time zone.

(1) Collection of Urine Specimens

Urine specimens were provided in the same manner as in (1) in Example 1-2, except that an oral medicine containing 400 mg of DMSA (DMSA 100MG, NuVision Inc.) was administered orally to five subjects. The target time zone was set to 0 to 6 hours after the administration. From each of the subjects, urines 0 to 6 hours after the administration were collected and accumulated to provide urine specimens.

(2) Analysis of Analytes

Regarding each of the urine specimens, the concentrations of arsenic, barium, cadmium, cesium, lead, mercury, nickel, thallium, tin, and tungsten as analytes and the concentration of creatinine were measured in the same manner as in (2) in Example 1-2. As described above, the measurement of the concentrations of the analytes and the creatinine was outsourced to Doctor's Data, Inc. Subsequently, the concentrations of the analytes were divided with the corresponding creatinine concentrations to calculate the corrected concentrations of the analytes. Then, on the basis of the data obtained regarding the urine specimens, the correlation equation expressing the correlation between the creatinine-corrected concentrations in each predetermined time zone and the creatinine-corrected concentrations in the target time zone was determined, and the correlation coefficient was calculated.

The results thereof are shown in Table 3. As can be seen from Table 3, when the analyte was arsenic, barium, cadmium, cesium, lead, mercury, nickel, thallium, tin, or tungsten, the measured amounts (y) of the analyte in the urine specimens collected in each predetermined time zone exhibited a high correlation with the true measured amounts (x) of the analyte. Also, estimated measured amounts of the analyte were predicted from the measured amounts of the analyte in the urine specimens collected in each predetermined time zone on the basis of the corresponding correlation equation. As a result, the estimated measured amounts of the analyte were very similar to the corresponding true measured amounts of the analyte. From these results, it was found that the measured amount of an analyte in a urine specimen collected in a predetermined time zone shows a high correlation with the measured amount of an analyte in a urine specimen collected in another time zone. It was also found that the amount of an analyte in a urine specimen collected in a target time zone can be predicted on the basis of the correlation between the measured amount of the analyte in a urine specimen collected in a predetermined time zone and the measured amount of the analyte in a urine specimen collected in a target time zone.

TABLE 3

|  | Correlation coefficient (correlation equation) for 0 to 1 hr | Correlation coefficient (correlation equation) for 0 to 2 hr | Correlation coefficient (correlation equation) for 0 to 3 hr |
|---|---|---|---|
| Arsenic (As) | 0.970 ($y = 0.8824x + 10.609$) | 0.992 ($y = 0.991x + 4.723$) | 0.997 ($y = 1.029x + 1.875$) |
| Barium (Ba) | 0.720 ($y = 1.1873x + 0.3464$) | 0.843 ($y = 1.127x + 0.170$) | 0.887 ($y = 1.075x + 0.092$) |
| Cadmium (Cd) | 0.824 ($y = 1.2308x − 0.1615$) | 0.850 ($y = 1.360x − 0.207$) | 0.868 ($y = 1.285x − 0.188$) |
| Cesium (Cs) | 0.969 ($0.8241x + 1.5875$) | 0.981 ($y = 1.190x − 0.305$) | 0.991 ($y = 1.167x − 0.330$) |
| Lead (Pb) | 0.823 ($y = 0.4366x + 1.9547$) | 0.891 ($y = 0.611x + 2.168$) | 0.968 ($y = 0.743x + 1.664$) |
| Mercury (Hg) | 0.946 ($y = 1.3732x + 3.5027$) | 0.975 ($y = 1.4562x + 3.4216$) | 0.973 ($y = 1.3243x + 2.9289$) |
| Nickel (Ni) | 0.721 ($y = 0.8178x + 0.4555$) | 0.798 ($y = 0.992x − 0.068$) | 0.835 ($y = 0.956x − 0.052$) |
| Thallium (Tl) | 0.612 ($y = 0.375x + 0.275$) | 0.886 ($y = 1.156x − 0.003$) | 0.904 ($y = 1.182x − 0.016$) |
| Tin (Sn) | 0.584 ($y = 0.325x + 0.305$) | 0.933 ($y = 0.828x + 0.128$) | 0.990 ($y = 1.025x + 0.035$) |
| Tungsten (W) | — | — | 0.656 ($y = 0.274x + 0.656$) |

Example 2

The present example examined whether the measured amounts of analytes in urine specimens collected in predetermined time zones after administration of a chelating agent correlate with the measured amounts of the analytes in urine specimens collected in a time zone different from the predetermined time zones.

Example 2-1

Example 2-1 examined whether the measured amounts of analytes in urine specimens collected in predetermined time zones after administration of EDTA correlate with the measured amounts of the analytes in urine specimens collected in a target time zone.

(1) Collection of Urine Specimens

Urine specimens were provided in the same manner as in (1) in Example 1-1, except that, from each of the subjects, urines in predetermined time zones (0 to 0.5 hours, 0.5 to 1 hour, 1 to 1.5 hours, 1.5 to 2 hours, and 2 to 6 hours) after the instillation were collected and accumulated. The target time zone was set to 0 to 6 hours after the instillation. From each of the subjects, urines 0 to 6 hours after the instillation were collected and accumulated to provide urine specimens.

(2) Analysis of Analytes

Regarding each of the urine specimens, the concentrations of lead and mercury as analytes and the concentration of creatinine were measured in the same manner as in (2) in Example 1-1. As described above, the measurement of the lead concentration and the creatinine concentration was outsourced to FALCO HOLDINGS Co., Ltd. Subsequently, the concentrations of the analytes were divided with the corresponding creatinine concentrations to calculate the corrected concentrations of the analytes. Then, the correlation equation expressing the correlation between the creatinine-corrected concentrations in each predetermined time zone and the creatinine-corrected concentrations in the target time zone was determined, and the correlation coefficient was calculated.

The results thereof are shown in Table 4. As can be seen from Table 4, when the analyte was mercury or lead, the measured amounts (y) of the analyte in the urine specimens collected in each predetermined time zone exhibited a high correlation with the true measured amounts (x) of the analyte. Also, estimated measured amounts of the analyte were predicted from the measured amounts of the analyte in the urine specimens collected in each predetermined time zone on the basis of the corresponding correlation equation. As a result, the estimated measured amounts of the analyte were very similar to the corresponding true measured amounts of the analyte. From these results, it was found that the measured amount of an analyte in a urine specimen collected in a predetermined time zone shows a high correlation with the measured amount of an analyte in a urine specimen collected in another time zone. It was also found that the amount of an analyte in a urine specimen collected in a target time zone can be predicted on the basis of the correlation between the measured amount of the analyte in a urine specimen collected in a predetermined time zone and the measured amount of the analyte in a urine specimen collected in a target time zone. Moreover, from the fact that the measured amount in any of the predetermined time zones exhibited a high correlation with the measured amount in the target time zone, it was found that, for example, from the measured amount of an analyte in a urine specimen collected in any time zone after the administration of a chelating agent, it is possible to predict the measured amount of the analyte in a urine specimen collected in any other time zone after the administration of the chelating agent.

TABLE 4

|  | Correlation coefficient (correlation equation) for 0 to hr 0.5 hr | Correlation coefficient (correlation equation) for 0.5 to 1 hr | Correlation coefficient (correlation equation) for 1 to 1.5 hr |
|---|---|---|---|
| Mercury (Hg) | 0.961 ($y = 2.357x − 2.336$) | 0.980 ($y = 6.870x − 3.205$) | 0.950 ($y = 2.496x − 0.660$) |
| Lead (Pb) | 0.718 ($y = 0.322x + 0.677$) | 0.593 ($y = 0.598x + 13.283$) | 0.808 ($y = 2.797x − 21.078$) |

|  | Correlation coefficient (correlation equation) for 1.5 to 2 hr Correlation coefficient (correlation equation) for 0 to 0.5 hr | Correlation coefficient (correlation equation) for 2 to 6 hr Correlation coefficient (correlation equation) for 0.5 to 1 hr | Correlation coefficient (correlation equation) for 1 to 1.5 hr |
|---|---|---|---|
| Mercury (Hg) | 0.867 ($y = 0.522x − 0.220$) | 0.662 ($y = 0.133x − 0.200$) |  |
| Lead (Pb) | 0.797 ($y = 1.941x − 12.556$) | 0.865 ($y = 0.871x + 2.108$) |  |

Example 2-2

Example 2-2 examined whether the measured amounts of analytes in urine specimens collected in predetermined time zones after administration of tiopronin correlate with the measured amounts of the analytes in urine specimens collected in a target time zone.

(1) Collection of Urine Specimens

Urine specimens were provided in the same manner as in (1) in Example 1-2, except that, from each of the subjects, urines in predetermined time zones (0 to 1 hour, 1 to 2 hours, 2 to 3 hours, and 3 to 6 hours) after the instillation were collected and accumulated. The target time zone was set to 0 to 6 hours after the instillation. From each of the subjects, urines 0 to 6 hours after the instillation were collected and accumulated to provide urine specimens.

(2) Analysis of Analytes

Regarding each of the urine specimens, the concentrations of aluminum, arsenic, barium, cadmium, cesium, mercury, nickel, thallium, tin, and tungsten as analytes and the concentration of creatinine were measured in the same manner as in (2) in Example 1-2. As described above, the measurement of the concentrations of the analytes and the creatinine was outsourced to Doctor's Data, Inc. Subsequently, the concentrations of the analytes were divided with the corresponding creatinine concentrations to calculate the corrected concentrations of the analytes. Then, the correlation equation expressing the correlation between the creatinine-corrected concentrations in each predetermined time zone and the creatinine-corrected concentrations in the target time zone was determined, and the correlation coefficient was calculated.

The results thereof are shown in Table 5. As can be seen from Table 5, when the analyte was aluminum, arsenic, barium, cadmium, cesium, mercury, nickel, thallium, tin, or tungsten, the measured amounts (y) of the analyte in the urine specimens collected in each predetermined time zone exhibited a high correlation with the true measured amounts (x) of the analyte. Also, estimated measured amounts of the analyte were predicted from the measured amounts of the analyte in the urine specimens collected in each predetermined time zone on the basis of the corresponding correlation equation. As a result, the estimated measured amounts of the analyte were very similar to the corresponding true measured amounts of the analyte. From these results, it was found that the measured amount of an analyte in a urine specimen collected in a predetermined time zone shows a high correlation with the measured amount of an analyte in a urine specimen collected in another time zone. It was also found that the amount of an analyte in a urine specimen collected in a target time zone can be predicted on the basis of the correlation between the measured amount of the analyte in a urine specimen collected in a predetermined time zone and the measured amount of the analyte in a urine specimen collected in a target time zone. Moreover, from the fact that the measured amount in any of the predetermined time zones exhibited a high correlation with the measured amount in the target time zone, it was found that, for example, from the measured amount of an analyte in a urine specimen collected in any time zone after the administration of a chelating agent, it is possible to predict the measured amount of the analyte in a urine specimen collected in any other time zone after the administration of the chelating agent.

TABLE 5

| | Correlation coefficient (correlation equation) for 0 to 1 hr | Correlation coefficient (correlation equation) for 1 to 2 hr | Correlation coefficient (correlation equation) for 2 to 3 hr | Correlation coefficient (correlation equation) for 3 to 6 hr |
|---|---|---|---|---|
| Aluminum (Al) | — | 0.782 (y = 1.617x + 0.118) | — | — |
| Arsenic (As) | 0.957 (y = 1.049x + 3.711) | 0.992 (y = 0.979x + 7.596) | 0.999 (y = 0.901x + 5.233) | 0.996 (y = 1.025x − 5.283) |
| Barium (Ba) | 0.866 (y = 0.802x + 0.526) | 0.924 (y = 1.249x + 0.081) | — | 0.983 (y = 1.167x − 0.512) |
| Cadmium (Cd) | 0.852 (y = 1.143x + 0.189) | 0.894 (y = 1.929x − 0.404) | 0.811 (y = 1.357x − 0.039) | 0.638 (y = 0.620x + 0.042) |
| Cesium (Cs) | 0.927 (y = 0.922x − 1.204) | 0.917 (y = 1.110x + 0.320) | 0.885 (y = 0.870x + 1.217) | 0.930 (y = 1.019x − 0.785) |
| Mercury (Hg) | 0.857 (y = 2.683x + 0.746) | 0.989 (y = 2.414x − 25.780) | 0.800 (y = 0.447x + 5.662) | — |
| Nickel (Ni) | 0.805 (y = 0.952x + 0.558) | 0.796 (y = 1.169x + 0.356) | 0.812 (y = 1.430x − 0.356) | 0.712 (y = 0.829x − 0.169) |
| Thallium (Tl) | 1.000 (y = 1.000x + 0.100) | 0.869 (y = 0.813x + 0.088) | 1.000 (y = 1.000x) | 0.991 (y = 1.093x − 0.074) |
| Tin (Sn) | 0.899 (y = 1.333x − 0.007) | 0.609 (y = 0.667x + 0.207) | 0.569 (y = 1.167x + 0.127) | 0.872 (y = 0.561x + 0.005) |
| Tungsten (W) | 0.980 (y = 1.819x − 0.038) | 0.980 (y = 1.415x − 0.030) | 0.979 (y = 0.936x + 0.028) | 0.948 (y = 0.635x + 0.022) |

Example 2-3

Example 2-3 examined whether the measured amounts of analytes in urine specimens collected in predetermined time zones after administration of DMSA correlate with the measured amounts of the analytes in urine specimens collected in a target time zone.

(1) Collection of Urine Specimens

Urine specimens were provided in the same manner as in (1) in Example 1-3, except that, from each of the subjects, urines in predetermined time zones (0 to 1 hour, 1 to 2 hours, 2 to 3 hours, and 3 to 6 hours) after the instillation were collected and accumulated. The target time zone was set to 0 to 6 hours after the instillation. From each of the subjects, urines 0 to 6 hours after the instillation were collected and accumulated to provide urine specimens.

(2) Analysis of Analytes

Regarding each of the urine specimens, the concentrations of aluminum, arsenic, barium, cadmium, cesium, lead, mercury, nickel, thallium, tin, and tungsten as analytes and the concentration of creatinine were measured in the same manner as in (2) in Example 1-2. As described above, the measurement of the concentrations of the analytes and the creatinine was outsourced to Doctor's Data, Inc. Subsequently, the concentrations of the analytes were divided with the corresponding creatinine concentrations to calculate the corrected concentrations of the analytes. Then, the correlation equation expressing the correlation between the creatinine-corrected concentrations in each predetermined time zone and the creatinine-corrected concentrations in the target time zone was determined, and the correlation coefficient was calculated.

The results thereof are shown in Table 6. As can be seen from Table 6, when the analyte was aluminum, arsenic, barium, cadmium, cesium, lead, mercury, nickel, thallium, tin, or tungsten, the measured amounts (y) of the analyte in the urine specimens collected in each predetermined time zone exhibited a high correlation with the true measured amounts (x) of the analyte. Also, estimated measured amounts of the analyte were predicted from the measured amounts of the analyte in the urine specimens collected in each predetermined time zone on the basis of the corresponding correlation equation. As a result, the estimated measured amounts of the analyte were very similar to the corresponding true measured amounts of the analyte. From these results, it was found that the measured amount of an analyte in a urine specimen collected in a predetermined time zone shows a high correlation with the measured amount of an analyte in a urine specimen collected in another time zone. It was also found that the amount of an analyte in a urine specimen collected in a target time zone can be predicted on the basis of the correlation between the measured amount of the analyte in a urine specimen collected in a predetermined time zone and the measured amount of the analyte in a urine specimen collected in a target time zone. Moreover, from the fact that the measured amount in any of the predetermined time zones exhibited a high correlation with the measured amount in the target time zone, it was found that, for example, from the measured amount of an analyte in a urine specimen collected in any time zone after the administration of a chelating agent, it is possible to predict the measured amount of the analyte in a urine specimen collected in any other time zone after the administration of the chelating agent.

TABLE 6

| | Correlation coefficient (correlation equation) for 0 to 1 hr | Correlation coefficient (correlation equation) for 1 to 2 hr | Correlation coefficient (correlation equation) for 2 to 3 hr | Correlation coefficient (correlation equation) for 3 to 6 hr |
|---|---|---|---|---|
| Aluminum (Al) | — | — | 0.610 (y = 0.346x − 1.543) | 0.843 (y = 1.506x + 0.569) |
| Arsenic (As) | 0.970 (y = 0.882x + 10.609) | 0.999 (y = 1.113x − 2.101) | 0.998 (y = 1.119x − 4.683) | 0.996 (y = 0.970x − 1.729) |
| Barium (Ba) | 0.720 (y = 1.187x + 0.346) | 0.908 (y = 1.002x − 0.022) | 0.949 (y = 0.936x − 0.068) | 0.888 (y = 0.928x − 0.054) |
| Cadmium (Cd) | 0.824 (y = 1.231x − 0.162) | 0.845 (y = 1.500x − 0.250) | 0.908 (y = 1.115x − 0.141) | 0.751 (y = 0.744x + 0.160) |
| Cesium (Cs) | 0.969 (y = 0.824x + 1.588) | 0.955 (y = 1.614x − 2.467) | 0.987 (y = 1.086x − 0.204) | 0.982 (y = 0.925x − 0.167) |
| Lead (Pb) | 0.823 (y = 0.437x + 1.955) | 0.930 (y = 0.986x + 1.835) | 0.982 (y = 1.059x + 0.493) | 0.986 (y = 1.229x − 1.569) |
| Mercury (Hg) | 0.946 (y = 1.373x + 3.503) | 0.961 (y = 1.635x + 2.852) | 0.938 (y = 1.008x + 2.375) | 0.941 (y = 0.770x − 3.115) |
| Nickel (Ni) | 0.721 (y = 0.818x + 0.455) | 0.860 (y = 1.202x − 0.730) | 0.904 (y = 0.877x − 0.045) | 0.848 (y = 1.033x + 0.116) |
| Thallium (Tl) | 0.612 (y = 0.375x + 0.275) | 0.930 (y = 2.000x − 0.300) | 0.913 (y = 1.250x − 0.050) | 0.833 (y = 0.874x − 0.006) |
| Tin (Sn) | 0.584 (y = 0.325x + 0.305) | 0.989 (y = 1.354x − 0.054) | 0.960 (y = 1.481x − 0.177) | 0.986 (y = 0.969x − 0.030) |
| Tungsten (W) | — | — | 0.612 (y = 0.750x + 0.025) | 1.000 (y = 1.672x + 0.000) |

While the present invention has been described above with reference to embodiments and examples, the present invention is by no means limited thereto. Various changes and modifications that may become apparent to those skilled in the art may be made in the configuration and specifics of the present invention without departing from the scope of the present invention.

This application is based upon and claims the benefit of priority from Japanese Patent Application No. 2015-059887 filed on Mar. 23, 2015, the disclosure of which is incorporated herein its entirety by reference.

INDUSTRIAL APPLICABILITY

According to the prediction method of the present invention, it is possible to easily predict the amount of an analyte in a urine specimen in a target time zone after administration of a chelating agent. Thus, the present invention is very useful in the fields of clinical practice etc., for example.

What is claimed is:

1. A method for predicting an amount of a metal in urine collected from a subject during a target time period, the method comprising:
    administering a chelating agent for chelating the metal to the subject;
    measuring an amount of the metal in urine collected for a predetermined time period of 0.1 to 3 hours from the subject within 0 to 6 hours after administering the chelating agent to the subject; and
    correlating the measured amount of the metal in urine collected for the predetermined time period from the subject with an amount predicted to be collected in urine from the subject during the target time period based upon a correlation equation that correlates an amount of metal measured in urine collected from a plurality of subjects during the predetermined time period after administering the chelating agent to the plurality of subjects to an amount of metal measured in urine collected from the plurality of subjects during the target time period, wherein the target time period is a period starting from administering the chelating agent and ending at from 6 to 24 hours after administering the chelating agent.

2. The method according to claim 1, wherein the amount of the metal is an amount of the metal relative to an internal standard in the urine specimen.

3. The method according to claim 1, wherein the amount of the metal is a weight of the metal.

4. The method according to claim 1, wherein the chelating agent is at least one chelating agent selected from the group consisting of dithizone, tiopronin, meso-2,3-dimercaptosuccinic acid, 2,3-dimercapto-1-propanesulfonic acid sodium salt, ethylenediaminetetraacetic acid, nitrilotriacetic acid, ethylene diamine-N,N'-disuccinic acid, α-lipoic acid, diethylenetriaminepentaacetic acid (DTPA), penicillamine, dimercaprol, glutathione, phytic acid, chitosan, citric acid, quercetin, and ascorbic acid.

5. The method according to claim 1, wherein the metal is at least one metal selected from the group consisting of aluminum, antimony, arsenic, barium, beryllium, bismuth, cadmium, cesium, gadolinium, lead, mercury, nickel, palladium, platinum, tellurium, thallium, thorium, tin, tungsten, and uranium.

* * * * *

UNITED STATES PATENT AND TRADEMARK OFFICE
CERTIFICATE OF CORRECTION

PATENT NO. : 11,237,153 B2
APPLICATION NO. : 15/077115
DATED : February 1, 2022
INVENTOR(S) : Masashi Uwabu It is certified that error appears in the above-identified patent and that said Letters Patent is hereby corrected as shown below:

On the Title Page

Column 2 (Other Publications), Line 15, delete "Dextoxification"," and insert --Detoxification",--.

Signed and Sealed this
Nineteenth Day of September, 2023

*Katherine Kelly Vidal*

Katherine Kelly Vidal
*Director of the United States Patent and Trademark Office*